United States Patent
Majeed et al.

(10) Patent No.: US 12,022,786 B2
(45) Date of Patent: Jul. 2, 2024

(54) METHOD OF ISOLATING SECONDARY METABOLITES FROM CAMBIUM DERIVED CALLUS CULTURES

(71) Applicants: Muhammed Majeed, Bangalore (IN); Kalyanam Nagabhushanam, East Windsor, NJ (US); Natarajan Sankaran, Bangalore (IN); Sivakumar Arumugam, Bangalore (IN); Muthuraman Gnanamani, Bangalore (IN); Kulithalai Viswanathan Krishnamurthy, Bangalore (IN); Ugraiah Amilineni, Bangalore (IN)

(72) Inventors: Muhammed Majeed, Bangalore (IN); Kalyanam Nagabhushanam, East Windsor, NJ (US); Natarajan Sankaran, Bangalore (IN); Sivakumar Arumugam, Bangalore (IN); Muthuraman Gnanamani, Bangalore (IN); Kulithalai Viswanathan Krishnamurthy, Bangalore (IN); Ugraiah Amilineni, Bangalore (IN)

( * ) Notice: Subject to any disclaimer, the term of this patent is extended or adjusted under 35 U.S.C. 154(b) by 0 days.

(21) Appl. No.: 17/431,036

(22) PCT Filed: Feb. 14, 2020

(86) PCT No.: PCT/US2020/018201
§ 371 (c)(1),
(2) Date: Aug. 13, 2021

(87) PCT Pub. No.: WO2020/168141
PCT Pub. Date: Aug. 20, 2020

(65) Prior Publication Data
US 2022/0145244 A1   May 12, 2022

(51) Int. Cl.
*A01H 4/00* (2006.01)
*C12N 5/04* (2006.01)

(52) U.S. Cl.
CPC ............... *A01H 4/002* (2021.01); *C12N 5/04* (2013.01)

(58) Field of Classification Search
CPC .................................. C12N 5/04; A01H 4/002
USPC ........................................................ 435/422
See application file for complete search history.

(56) References Cited

U.S. PATENT DOCUMENTS

2008/0194025 A1 * 8/2008 Jin ........................... C12N 5/02
                                                                    435/420
2018/0370885 A1 * 12/2018 Majeed et al. .......... C07C 35/44

OTHER PUBLICATIONS

Kalola et al. Extraction and TLC Desitometric Determination of Triterpenoid Acids (Arjungenin, ARjunolic Acid) from Terminalia arjuna Stem Bark without interference of Tannins. Chromatographia 2006, 63 May (No. 9/10).*
Kalola et al. Chromatographia, 63 (No. 9/10): 475-481 (Year: 2006).*
Salim. Plant Archives, vol. 18, No. 2, pp. 2519-2527 (Year: 2018).*

* cited by examiner

*Primary Examiner* — Keith O. Robinson

(57) ABSTRACT

The present invention discloses a method of isolating secondary metabolites, specifically arjunolic acid, from the calli and/or the suspension cultures derived from the pluripotent cambium tissue of *Terminalia arjuna*. The invention also discloses a method of inducing callus, establishing and maintaining suspension cultures of callus derived from the cambium of *Terminalia arjuna* for the isolation of secondary metabolites.

7 Claims, 4 Drawing Sheets
(3 of 4 Drawing Sheet(s) Filed in Color)

METHOD OF ISOLATING SECONDARY METABOLITES FROM CAMBIUM DERIVED CALLUS CULTURES

CROSS-REFERENCE TO RELATED PATENT APPLICATION

This is a US national phase application of PCT application no. PCT/US20/18201 filed on 14 Feb. 2020, claiming priority from Indian Provisional Patent Application No. 201941005990 filed on 15 Feb. 2019, the details of which are being incorporated herein by reference.

BACKGROUND OF THE INVENTION

Field of the Invention

The present invention in general relates to the method of isolation of secondary metabolites from plants. More specifically, the present invention relates to a method isolating callus-derived cell lines from the cambial tissues of *Terminalia arjuna* and isolation of secondary metabolites using a continuous suspension culture method.

Description of Prior Art

Plants play a major role in the lives of human beings. In addition to being a good source of food, they also harbor many chemical substances that can be used for treating a variety of human diseases. There are many plants reported in the ancient Ayurvedic, Unani and Siddha texts that elicit medicinal properties. The recent advancements in science and technology have enabled us to specifically identify the active substance, called secondary metabolites, responsible for the biological activity of the plant. Plant secondary metabolites such as alkaloids, polyphenols, flavonoids, etc are characterized and isolated from the plant source for medicinal purposes. However, due to the limited availability of many of the medicinal plants, not many active secondary metabolites could be tapped for their therapeutic use.

The most common approach for obtaining these compounds is from their native source i.e. plants. However, this conventional process presents several disadvantages such as non-availability of these metabolites from plants throughout year, difficulty in plant cultivation and inconsistent product yield due to climatic variations etc. Difficulty to obtain sufficient amounts of desired plant material, their slow growth, varying composition and concentration depending upon the geographical position and climatic conditions coupled with low yield of isolated compounds are some of the limitations of commercial extraction of these compounds by using plants as a single resource. Further, the reckless collection of plants has put several of them under the categories of endangered or at the verge of extinction. This has prompted industries and scientists to find alternative technologies to produce plant natural products so that plants can be preserved.

With the advent of tissue culture techniques, many rare species of medicinal plants were grown in-vitro and exploited for their therapeutic potential. However, with the increase in population, the demand for the availability of specific secondary metabolites has increased. Cell culture techniques, wherein the secondary metabolites are continuously isolated by growing pluripotent plant cells in suspension cultures with unlimited supply of growth media are now being employed for large scale production and isolation of plant secondary metabolites. These Cambial meristematic cells (CMCs) would increase phytochemical production dramatically after hours of elicited stress. This is because plant CMCs are immortal, highly stress-resistant, and have the whole genome of plant. The elicited stress will activate the gene cluster involved in phytochemicals synthesis in the CMC. Cambial cultivation would also prevent destructive harvesting of bark and wood for getting desired phytochemicals.

Different processes have been developed to isolate specific metabolites from diverse plant species. U.S. Pat. No. 8,017,397 discloses a process of culturing callus of *Taxus* sp. from the cambial tissue and isolation of metabolite taxol from the callus. The patent also discloses a method of continuous isolation of taxol using a bioreactor-based suspension culture. Similarly, U.S. Pat. No. 8,247,230 discloses a method of isolating plant cell line derived from the cambium of wild ginseng. Since, the characteristic features are not the same for two species of a plant, the method of isolating cell lines (callus) from the cambial tissue differ from plant to plant. Moreover, the method of isolating specific secondary metabolite from the same plant species is also different. Thus, the present invention discloses a novel and non-obvious method of isolating callus-derived cell lines from the cambial tissues of *Terminalia arjuna* and isolation of secondary metabolites from the same using a continuous suspension culture method.

*Terminalia arjuna* or *arjuna* is a well-known medicinal plant used in the ancient Ayurvedic medicine. The bark of *Terminalia arjuna* is reported to contain many bioactive compounds like Arjunic acid, Arjunolic acid, Arjungenin, Arjunetin, Arjunoglucoside-I, Arjunoglucoside-II, Asiatic acid, Catechin and Gallocatechin, which can be tapped for use in the treatment of many diseases. Arjunoglucoside is a potent cardio protective agent and is also reported to have anticancer, hepatoprotective, antiviral, antioxidant, anti-asthmatic, anti-fertility, anti-diabetic, wound healing, anti-platelet and anticoagulant, anti-bacterial and anti-fungal activity. (Saxena et al., Cytotoxic agents from *Terminalia arjuna*, Planta Med. 2007; 73(14):1486-90). Another compound—Arjunolic acid is reported to be a potent antioxidant and free radicle scavenger. It exhibits therapeutic effects like prevention of myocardial necrosis, platelet aggregation and coagulation and lowering of blood pressure, heart rate and cholesterol levels (Hemalatha et al., Indian J Exp Biol. 2010 March; 48(3):238-47).

Different processes exist for the isolation of secondary metabolites from *Terminalia arjuna*. U.S. Pat. No. 10,479, 749 B2 discloses a process for isolation and enrichment of bioactive compounds Arjunic acid, Arjunolic acid, Arjungenin, Arjunetin, Arjunoglucoside-I, Arjunoglucoside-II, and Catechin from the bark of *Terminalia arjuna*. The invention also discloses a composition standardized to contain 3% arjunoglucosides isolated from the bark of *Terminalia arjuna*. Owing, to the reasons mentioned in the aforesaid paragraphs on the shortcomings of isolating secondary metabolites from bark of the plant, there exists an industrial need for developing of a continuous process for the isolation of secondary metabolites from *Terminalia arjuna*. The present invention solves the above-mentioned problem by disclosing a process for isolating secondary metabolites, specifically arjunolic acid, from callus-derived cell lines from the cambial tissues of *Terminalia arjuna*.

It is the principle object of the invention to disclose a method for isolating arjunolic acid from callus-derived cell lines from the cambial tissues of *Terminalia arjuna*.

It is another object of the invention to disclose a method for isolating and inducing pluripotent cell line from the callus derived from the cambium of *Terminalia arjuna*.

In is yet another object of the invention to disclose a method for developing and maintaining suspension cultures of pluripotent cell line from the callus derived from the cambium of *Terminalia arjuna*.

The present invention fulfills this objective and provided further related advantages.

SUMMARY OF THE INVENTION

In the most preferred embodiment, the invention discloses a method for inducing pluripotent cell line from the callus derived from the cambium of *Terminalia arjuna*.

In another preferred embodiment, the invention discloses a method of establishing and maintaining suspension cultures of pluripotent cell line from the callus derived from the cambium of *Terminalia arjuna*.

In another preferred embodiment, the invention discloses a method of isolating secondary metabolites from the suspension cultures of pluripotent cell line from the callus derived from the cambium of *Terminalia arjuna*. More specifically, the invention discloses a method of isolating arjunolic acid from the suspension cultures of pluripotent cell line from the callus derived from the cambium of *Terminalia arjuna*.

Other features and advantages of the present invention will become apparent from the following more detailed description, taken in conjunction with the accompanying images, which illustrate, by way of example, the principle of the invention.

BRIEF DESCRIPTION OF DRAWINGS

The patent or application file contains at least one drawing executed in color. Copies of this patent or patent application publication with color drawing(s) will be provided by the office upon request and payment of the necessary fee.

DETAILED DESCRIPTION OF THE MOST PREFERRED EMBODIMENT

Figure 1:
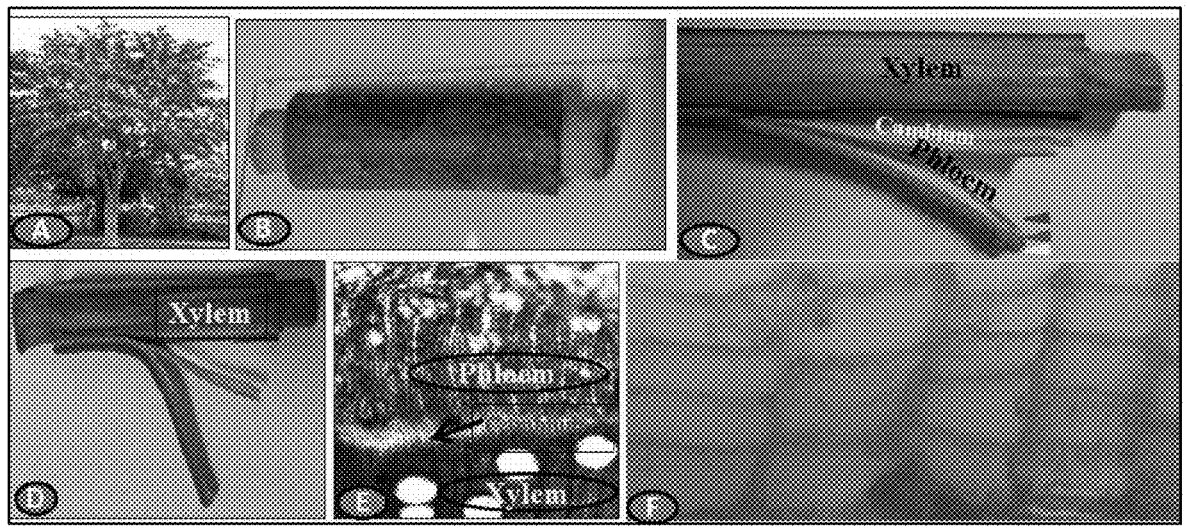
FIG. 1 shows the general process for the isolation of cambial tissue in *Terminalia arjuna*. (a) Naturally growing *T. arjuna* tree, (b) Twigs collected from a small branch of the tree, (c) Preparation of *T. arjuna* explant by peeling off cambium, phloem, cortex and epidermal cells from the xylem. Cell types are indicated by the following colored arrows: orange, xylem; green, cambium; red, phloem; blue, cortex; and yellow, epidermis. (d) Separated xylem and pith tissue from stem segment in panel D, stained with lignin-specific dye phloroglucinol-HCl, (Note: phloroglucinol-HCl (0.5% w/v) did not stain other tissues), (e) T.S of Stem showing the location of cambial tissue and (f) Cambial tissues enlarged.

In the most preferred embodiment, the invention discloses a method of inducing pluripotent cell line from the callus derived from the cambium of *Terminalia arjuna*, said method comprising steps of:
a) Washing the *Terminalia arjuna* twigs (15-20 mm diameter) in tap water followed by Tween 20 wash;
b) Incubating the washed *Terminalia arjuna* twigs in distilled water containing 10-50 mg/L ascorbic acid for 15-30 minutes, to avoid subsequent phenolic oxidation and browning of callus before its induction;
c) Treating the twig pieces of *Terminalia arjuna* with disinfecting solution for 1-5 minutes and rinsing in sterile distilled water;
d) Separating the cambium layer from the treated twigs and inoculating the cambial explants in the culture bottles containing medium combined with specific inducers and growth regulators along with sucrose and agar, with xylem side (phloem side is avoided) in contact with the medium;
e) Incubating the culture bottles at 23-27° C. under 2,000-2,500 lux of white fluorescent light for 16 h/day for induction of callus;
f) Sub-culturing the callus after 15 days of inoculation, followed by a second sub-culture after 45 days of inoculation and third subculture after 90 days of inoculation to yield friable calli after a period of 120 days of inoculation.

In a related aspect, the disinfectant is selected from the group comprising, but not limited to, calcium hypochlorite, sodium hypochlorite, hydrogen peroxide, ethanol, silver nitrate, mercuric chloride, benzalkonium chloride. In a related aspect, the culture medium is selected from the group comprising Murashige & Skoog (MS) medium, modified Gamborg's B5 (mB5) medium, Lloyed & McCown (WPM) medium, Schenk & Hildebrand (SM) medium, Quoirin & LepioVre (LP) medium and Allen's medium. In a preferred aspect, the culture medium of is WPM medium. In another related aspect, the inducers and growth regulators selected from the group comprising Indole acetic acid (IAA), Indole butyric acid (IBA), Picloram, p-Chlorophenoxyacetic acid (CPA), 2,4-Dichlorophenoxyacetic acid (2,4-D), Naphthaleneacetic acid (NAA), tender coconut water, banana powder. In preferred aspect, the inducer and growth regulator is 2,4-Dichlorophenoxyacetic acid (2,4-D). In another preferred aspect, the inducer and growth regulator 2,4-Dichlorophenoxyacetic acid is added at a concentration of 1 mg/L.

In another preferred embodiment, the invention discloses a method of establishing and maintaining suspension cultures of pluripotent cell line from the callus derived from the cambium of *Terminalia arjuna*, said method comprising steps of:
a) Washing the *Terminalia arjuna* twigs (15-20 mm diameter) in tap water followed by Tween 20 wash;
b) Incubating the washed *Terminalia arjuna* twigs in distilled water containing 10-50 mg/L ascorbic acid for 15-30 minutes, to avoid subsequent phenolic oxidation and browning of callus before its induction;
c) Treating the twig pieces of *Terminalia arjuna* with disinfecting solution for 1-5 minutes and rinsing in sterile distilled water;
d) Separating the cambium layer from the treated twigs and inoculating the cambial explants in the culture bottles containing medium combined with specific inducers and growth regulators along with sucrose and agar, with xylem side (phloem side is avoided) in contact with the medium;
e) Incubating the culture bottles at 23-27° C. under 2,000-2,500 lux of white florescent light for 16 h/day for induction of callus;
f) Sub-culturing the callus after 15 days of inoculation, followed by a second sub-culture after 45 days of inoculation and third subculture after 90 days of inoculation to yield friable calli after a period of 120 days of inoculation;
g) Transferring the friable callii into a conical flasks or airlift bioreactor containing culture medium, growth regulators and sucrose maintained at 25±2° C., with a light intensity of ~2500 lux under a photoperiod of 16/8 h (light/dark) with continuous shaking (at 120 rpm) in the conical flasks or aeration in the air lift bioreactor, respectively, for a period of 4 weeks;
h) Filtering the cultures using 250 μm Nylon filters for use as an inoculum;
i) Transferring 20% inoculum into individual conical flasks containing liquid media containing growth regulators and incubating at 25±2° C., at 120 rpm, with a light intensity of ~2500 lux under a photoperiod of 16/8 h (light/dark) with continuous shaking for a period of 1-4 weeks for evaluating the biomass production;
j) Separating the cells after three weeks of incubation and adding equal volume of pre-treated media comprising of 1.0 M mannitol in liquid medium with growth regulators and incubated for 2-3 days with 120 rpm at 25±2° C. in dark;
k) Separating the cells from the pre-treated culture of step j) and replacing the supernatant with equal volume of cryoprotectant solution comprising 2.0 M sucrose, 1.0 M glycerol, 1.0 M DMSO and 1% L-proline (w/v);
l) Incubating at 4° C. for 1 h with intermittent shaking followed by freezing at −80° C. for long term storage.

In a related aspect, the disinfectant is selected from the group comprising, but not limited to, calcium hypochlorite, sodium hypochlorite, hydrogen peroxide, ethanol, silver nitrate, mercuric chloride, benzalkonium chloride. In a related aspect, the culture medium is selected from the group comprising Murashige & Skoog (MS) medium, modified Gamborg's B5 (mB5) medium, Lloyed & McCown (WPM) medium, Schenk & Hildebrand (SM) medium, Quoirin & LepioVre (LP) medium and Allen's medium. In a preferred aspect, the culture medium of is WPM medium. In another related aspect, the inducers and growth regulators selected from the group comprising Indole acetic acid (IAA), Indole butyric acid (IBA), Picloram, p-Chlorophenoxyacetic acid (CPA), 2,4-Dichlorophenoxyacetic acid (2,4-D), Naphthaleneacetic acid (NAA), tender coconut water, banana powder. In preferred aspect, the inducer and growth regulator is 2,4-Dichlorophenoxyacetic acid (2,4-D). In another preferred aspect, the inducer and growth regulator 2,4-Dichlorophenoxyacetic acid is added at a concentration of 1 mg/L.

In another preferred embodiment, the invention discloses a method of isolating secondary metabolites from the suspension cultures of pluripotent cell line from the callus derived from the cambium of *Terminalia arjuna*, said method comprising steps of:
a) Washing the *Terminalia arjuna* twigs (15-20 mm diameter) in tap water followed by Tween 20 wash;
b) Incubating the washed *Terminalia arjuna* twigs in distilled water containing 10-50 mg/L ascorbic acid for 15-30 minutes, to avoid subsequent phenolic oxidation and browning of callus before its induction;
c) Treating the twig pieces of *Terminalia arjuna* with disinfecting solution for 1-5 minutes and rinsing in sterile distilled water;
d) Separating the cambium layer from the treated twigs and inoculating the cambial explants in the culture bottles containing medium combined with specific inducers and growth regulators along with sucrose and agar, with xylem side (phloem side is avoided) in contact with the medium;
e) Incubating the culture bottles at 23-27° C. under 2,000-2,500 lux of white florescent light for 16 h/day for induction of callus;
f) Sub-culturing the callus after 15 days of inoculation, followed by a second sub-culture after 45 days of inoculation and third subculture after 90 days of inoculation to yield friable calli after a period of 120 days of inoculation;
g) Transferring the friable callii into a conical flasks or airlift bioreactor containing culture medium, growth regulators and sucrose maintained at 25±2° C., with a light intensity of ~2500 lux under a photoperiod of 16/8 h (light/dark) with continuous shaking (at 120 rpm) in the conical flasks or aeration in the air lift bioreactor, respectively, for a period of 4 weeks;
h) Filtering the cultures using 250 μm Nylon filters for use as an inoculum;
i) Transferring 20% inoculum into individual conical flasks containing liquid media containing growth regulators and incubating at 25±2° C., at 120 rpm, with a light intensity of ~2500 lux under a photoperiod of 16/8 h (light/dark) with continuous shaking for a period of 1-4 weeks for evaluating the biomass production;
j) Separating the cells after three weeks of incubation and adding equal volume of pre-treated media comprising of 1.0 M mannitol in liquid medium with growth regulators and incubated for 2-3 days with 120 rpm at 25±2° C. in dark;
k) Separating the cells from the pre-treated culture of step j) and replacing the supernatant with equal volume of cryoprotectant solution comprising 2.0 M sucrose, 1.0 M glycerol, 1.0 M DMSO and 1% L-proline (w/v);
l) Incubating at 4° C. for 1 h with intermittent shaking followed by freezing at −80° C. for long term storage.
m) Separating the cells of step i) after three weeks of culture or re-culturing the frozen cells of step l) and extracting with solvent and/or super critical fluid extraction (SCFE) for the identification of secondary metabolites.

In a related aspect, the disinfectant is selected from the group comprising, but not limited to, calcium hypochlorite, sodium hypochlorite, hydrogen peroxide, ethanol, silver nitrate, mercuric chloride, benzalkonium chloride. In a related aspect, the culture medium is selected from the group comprising Murashige & Skoog (MS) medium, modified Gamborg's B5 (mB5) medium, Lloyed & McCown (WPM) medium, Schenk & Hildebrand (SM) medium, Quoirin & LepioVre (LP) medium and Allen's medium. In a preferred aspect, the culture medium is WPM medium. In another related aspect, the inducers and growth regulators selected from the group comprising Indole acetic acid (IAA), Indole butyric acid (IBA), Picloram, p-Chlorophenoxyacetic acid (CPA), 2,4-Dichlorophenoxyacetic acid (2,4-D), Naphthaleneacetic acid (NAA), tender coconut water, banana powder. In preferred aspect, the inducer and growth regulator is 2,4-Dichlorophenoxyacetic acid (2,4-D). In another preferred aspect, the inducer and growth regulator 2,4-Dichlorophenoxyacetic acid is added at a concentration of 1 mg/L. In a related embodiment, the secondary metabolite is selected from the group comprising of Arjunic acid, Arjunolic acid, Arjungenin, Arjunetin, Arjunoglucoside-I, Arjunoglucoside-II, Asiatic acid, Catechin and Gallocatechin.

In another preferred embodiment, the invention discloses a method of isolating arjunolic acid from the suspension cultures of pluripotent cell line from the callus derived from the cambium of *Terminalia arjuna*, said method comprising steps of:

a) Washing the *Terminalia arjuna* twigs (15-20 mm diameter) in tap water followed by Tween 20 wash;
b) Incubating the washed *Terminalia arjuna* twigs in distilled water containing 10-50 mg/L ascorbic acid for 15-30 minutes, to avoid subsequent phenolic oxidation and browning of callus before its induction;
c) Treating the twig pieces of *Terminalia arjuna* with disinfecting solution for 1-5 minutes and rinsing in sterile distilled water;
d) Separating the cambium layer from the treated twigs and inoculating the cambial explants in the culture bottles containing medium combined with specific inducers and growth regulators along with sucrose and agar, with xylem side (phloem side is avoided) in contact with the medium;
e) Incubating the culture bottles at 23-27° C. under 2,000-2,500 lux of white florescent light for 16 h/day for induction of callus;
f) Subculturing the callus after 15 days of inoculation, followed by a second sub-culture after 45 days of inoculation and third subculture after 90 days of inoculation to yield friable calli after a period of 120 days of inoculation;
g) Transferring the friable callii into a conical flasks or airlift bioreactor containing culture medium, growth regulators and sucrose maintained at 25±2° C., with a light intensity of ~2500 lux under a photoperiod of 16/8 h (light/dark) with continuous shaking (at 120 rpm) in the conical flasks or aeration in the air lift bioreactor, respectively, for a period of 4 weeks;
h) Filtering the cultures using 250 µm Nylon filters for use as an inoculum;
i) Transferring 20% inoculum into individual conical flasks containing liquid media containing growth regulators and incubating at 25±2° C., at 120 rpm, with a light intensity of ~2500 lux under a photoperiod of 16/8 h (light/dark) with continuous shaking for a period of 1-4 weeks for evaluating the biomass production;
j) Separating the cells after three weeks of incubation and adding equal volume of pre-treated media comprising of 1.0 M mannitol in liquid medium with growth regulators and incubated for 2-3 days with 120 rpm at 25±2° C. in dark;
k) Separating the cells from the pre-treated culture of step j) and replacing the supernatant with equal volume of cryoprotectant solution comprising 2.0 M sucrose, 1.0 M glycerol, 1.0 M DMSO and 1% L-proline (w/v);
l) Incubating at 4° C. for 1 h with intermittent shaking followed by freezing at −80° C. for long term storage.
m) Separating the cells of step i) after three weeks of culture or re-culturing the frozen cells of step l) and extracting with methanol followed by concentration for the identification of arjunolic acid by HPLC, HPTLC or NMR;
n) Separating the cells of step i) after three weeks of culture or re-culturing the frozen cells of step l), dried and charged into the extractor;
o) Extracting in Supercritical fluid $CO_2$ with 200-300 bar pressure along with ethanol 15% w/w entrainer at about 45-50° C. for 3-5 h to obtain S1 and S2 fractions;
p) Removing the residuals from the S1 fraction and extracting with hexane to obtain a hexane soluble and hexane insoluble layers;
q) Separating the hexane insoluble layer and extracting with ethyl acetate to obtain an ethyl acetate fraction and concentrated to half the volume;
r) Cooling the concentrated ethyl acetate fraction at about 5° C. for 12 hours;
s) Identifying the presence of arjunolic acid using HPLC, HPTLC or NMR.

In a related aspect, the disinfectant is selected from the group comprising, but not limited to, calcium hypochlorite, sodium hypochlorite, hydrogen peroxide, ethanol, silver nitrate, mercuric chloride, benzalkonium chloride. In a related aspect, the culture medium is selected from the group comprising Murashige & Skoog (MS) medium, modified Gamborg's B5 (mB5) medium, Lloyed & McCown (WPM) medium, Schenk & Hildebrand (SM) medium, Quoirin & LepioVre (LP) medium and Allen's medium. In a preferred aspect, the culture medium is WPM medium. In another related aspect, the inducers and growth regulators selected from the group comprising Indole acetic acid (IAA), Indole butyric acid (IBA), Picloram, p-Chlorophenoxyacetic acid (CPA), 2,4-Dichlorophenoxyacetic acid (2,4-D), Naphthaleneacetic acid (NAA), tender coconut water, banana powder. In preferred aspect, the inducer and growth regulator is 2,4-Dichlorophenoxyacetic acid (2,4-D). In another preferred aspect, the inducer and growth regulator 2,4-Dichlorophenoxyacetic acid is added at a concentration of 1 mg/L.

In another preferred embodiment, the invention discloses a composition comprising arjunolic acid, isolated from the suspension cultures of pluripotent cell line from the callus derived from the cambium of *Terminalia arjuna* using a process comprising steps of:

a) Washing the *Terminalia arjuna* twigs (15-20 mm diameter) in tap water followed by Tween 20 wash;
b) Incubating the washed *Terminalia arjuna* twigs in distilled water containing 10-50 mg/L ascorbic acid for 15-30 minutes, to avoid subsequent phenolic oxidation and browning of callus before its induction;
c) Treating the twig pieces of *Terminalia arjuna* with disinfecting solution for 1-5 minutes and rinsing in sterile distilled water;
d) Separating the cambium layer from the treated twigs and inoculating the cambial explants in the culture bottles containing medium combined with specific inducers and growth regulators along with sucrose and agar, with xylem side (phloem side is avoided) in contact with the medium;
e) Incubating the culture bottles at 23-27° C. under 2,000-2,500 lux of white florescent light for 16 h/day for induction of callus;
f) Sub-culturing the callus after 15 days of inoculation, followed by a second sub-culture after 45 days of inoculation and third subculture after 90 days of inoculation to yield friable calli after a period of 120 days of inoculation;
g) Transferring the friable callii into a conical flasks or airlift bioreactor containing culture medium, growth regulators and sucrose maintained at 25±2° C., with a light intensity of ~2500 lux under a photoperiod of 16/8 h (light/dark) with continuous shaking (at 120 rpm) in the conical flasks or aeration in the air lift bioreactor, respectively, for a period of 4 weeks;
h) Filtering the cultures using 250 μm Nylon filters for use as an inoculum;
i) Transferring 20% inoculum into individual conical flasks containing liquid media containing growth regulators and incubating at 25±2° C., at 120 rpm, with a light intensity of ~2500 lux under a photoperiod of 16/8 h (light/dark) with continuous shaking for a period of 1-4 weeks for evaluating the biomass production;
j) Separating the cells after three weeks of incubation and adding equal volume of pre-treated media comprising of 1.0 M mannitol in liquid medium with growth regulators and incubated for 2-3 days with 120 rpm at 25±2° C. in dark;
k) Separating the cells from the pre-treated culture of step j) and replacing the supernatant with equal volume of cryoprotectant solution comprising 2.0 M sucrose, 1.0 M glycerol, 1.0 M DMSO and 1% L-proline (w/v);
l) Incubating at 4° C. for 1 h with intermittent shaking followed by freezing at −80° C. for long term storage.
m) Separating the cells of step i) after three weeks of culture or re-culturing the frozen cells of step l) and extracting with methanol followed by concentration for the identification of arjunolic acid by HPLC, HPTLC or NMR;
n) Separating the cells of step i) after three weeks of culture or re-culturing the frozen cells of step l), dried and charged into the extractor;
o) Extracting in Supercritical fluid $CO_2$ with 200-300 bar pressure along with ethanol 15% w/w entrainer at about 45-50° C. for 3-5 h to obtain S1 and S2 fractions;
p) Removing the residuals from the S1 fraction and extracting with hexane to obtain a hexane soluble and hexane insoluble layers;
q) Separating the hexane insoluble layer and extracting with ethyl acetate to obtain an ethyl acetate fraction and concentrated to half the volume;
r) Cooling the concentrated ethyl acetate fraction at about 5° C. for 12 hours;
s) Identifying the presence of arjunolic acid using HPLC, HPTLC or NMR.

In a related aspect, the disinfectant is selected from the group comprising, but not limited to, calcium hypochlorite, sodium hypochlorite, hydrogen peroxide, ethanol, silver nitrate, mercuric chloride, benzalkonium chloride. In a related aspect, the culture medium is selected from the group comprising Murashige & Skoog (MS) medium, modified Gamborg's B5 (mB5) medium, Lloyed & McCown (WPM) medium, Schenk & Hildebrand (SM) medium, Quoirin & LepioVre (LP) medium and Allen's medium. In a preferred aspect, the culture medium is WPM medium. In another related aspect, the inducers and growth regulators selected from the group comprising Indole acetic acid (IAA), Indole butyric acid (IBA), Picloram, p-Chlorophenoxyacetic acid (CPA), 2,4-Dichlorophenoxyacetic acid (2,4-D), Naphthaleneacetic acid (NAA), tender coconut water, banana powder. In preferred aspect, the inducer and growth regulator is 2,4-Dichlorophenoxyacetic acid (2,4-D). In another preferred aspect, the inducer and growth regulator 2,4-Dichlorophenoxyacetic acid is added at a concentration of 1 mg/L.

The preferred embodiments of the invention are explained in detail in the following illustrative examples Example 1: Induction of Callus and Establishment of Suspension Culture Methodology Collection and Sterilization of Plant Twigs:

The twigs of (15-20 mm diameter) *Terminalia arjuna*, were regularly collected from 20 year old tree growing at Peenya in Bangalore and washed under tap water for 30 min. Disinfection was done by incubating the washed *Terminalia arjuna* twigs in distilled water containing 10-50 mg/L ascorbic acid for 15-30 minutes, to avoid subsequent phenolic oxidation and browning of callus before its induction and treating the twig pieces of *Terminalia arjuna* with Sodium hypochlorite for 1-5 minutes and rinsing in sterile distilled water.

Isolation & Inoculation of Cambium Layer:

For isolation of cambium meristematic cells (CMCs); cambium, phloem, cortex and epidermal tissue were peeled off from the xylem and from that a thin layer of cambium layer was peeled (FIG. 1). It was further confirmed by microscopy (FIG. 1F). The isolated cambium layer was cut into small pieces (approx. 1 cm size). The explants were inoculated on a solid medium in such a manner that xylem side faced the culture medium (i.e., in contact with the media) while the phloem side faced upwards. The explants were inoculated on different media with varying concentrations and combinations of plant growth regulators, keeping 30 g/L sucrose and 8 g/L agar in all of them. All the cultures were incubated at 25±2° C. under 2,000-2,500 lux of white fluorescent light for 16 h/day.

Standardization of Culture Medium and PGR's for the Production of Calli from Cambial Explants:

In the present study, we have used different media like Murashige & Skoog (MS medium), Gamborg's (B5 medium) and Woody plant medium (WPM) supplemented with different plant growth regulators (PGRs) like Picloram, 2,4-dichlorophenoxy acetic acid (2,4-D), Naphthalene acetic acid (NAA), Indole-3-butyric acid (IBA), Indole-3-acetic acid (IAA), 6-Benzylaminopurine (BAP) and Kinetin, individually and in combinations.

Influence of Light and Duration of Time on Callus and Secondary Metabolites Production:

The cambial explants were inoculated on the above-mentioned media and incubated in the dark (without light for 8 h) and with light for 16 h growth chambers separately at 25±2° C. After initiation of enough callus, it has been sub-cultured at every three weeks for further proliferation. Then the calli was tested for the presence of required secondary metabolites.

Suspension Culture

Suspension cultures were established by inoculating a sample of approx. 1 g of fresh callus of *T. arjuna* into a 250 ml Erlenmeyer conical flasks containing 100 ml of WPM liquid medium supplemented with 1 mg/L 2,4-D and the cultures were maintained at 25±2° C., at 120 rpm, with a light intensity of ~2500 lux under a photoperiod of 16/8 h (light/dark).

Results

Standardization of Culture Medium and Plant Growth Regulators to Produce Calli from Cambial Explants of *T. arjuna*:

Recently developed twigs collected from a wild grown *Terminalia arjuna* tree were used for the establishment of cambial culture. The twigs were surface sterilized and gently peeled off the tissue that contained cambium, phloem, cortex and epidermis from the xylem. Subsequently a thin layer of cambium was separated from the above tissue and confirmed the absence of xylem cells by staining with phloroglucinol-HCl, which detects lignin deposition (FIG. 1D). The cambium tissue was cultured on solid media containing different plant growth regulators (Table 1).

TABLE 1

Standardization of culture medium to produce callus from cambial explants of *T. arjuna*. (B5- Gamborg's, MS-Murashige & Skoog and WPM - Woody plant medium).

| Medium | PGRs | No. of explants inoculated | No. of explants showing response | % of response (after 45 days) | Average % of response |
|---|---|---|---|---|---|
| B5 | 1 mg/L picloram | 350 | 175 | 50 | 53 |
|  |  | 240 | 145 | 60 |  |
|  |  | 320 | 155 | 48 |  |
| MS | 2 mg/L 2,4-D | 200 | 80 | 40 | 43 |
|  |  | 233 | 115 | 49 |  |
|  |  | 240 | 100 | 42 |  |
| WPM | 1 mg/L 2,4-D | 120 | 98 | 81 | 80 |
|  |  | 220 | 175 | 79 |  |
|  |  | 255 | 206 | 80 |  |

Figure 2:
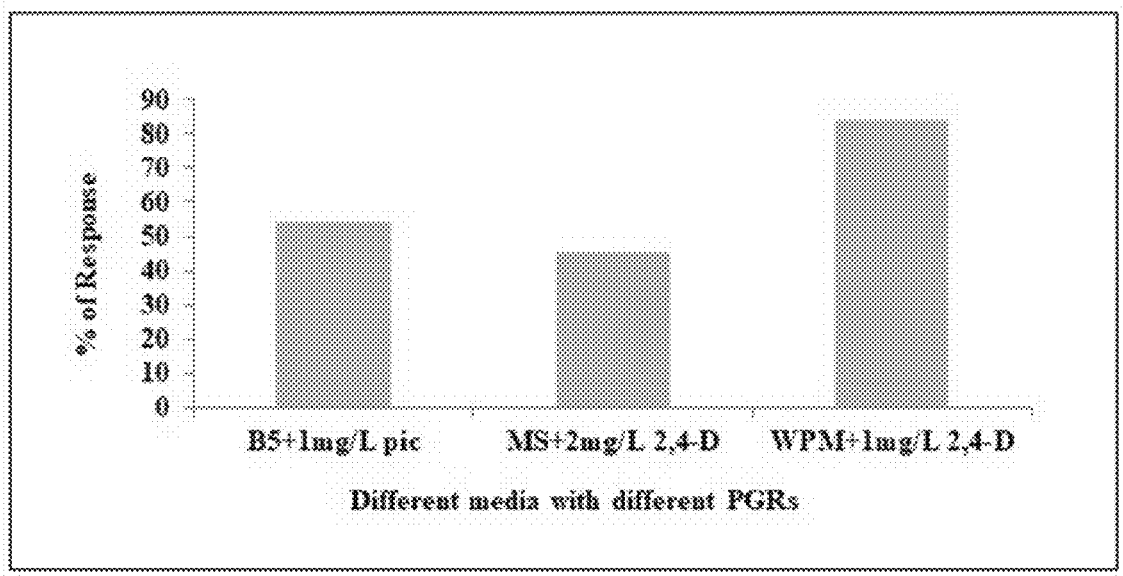
FIG. 2 is a graphical representation showing percentage of response in growth of cambial explants of *T. arjuna* for callus induction
Figure 3:
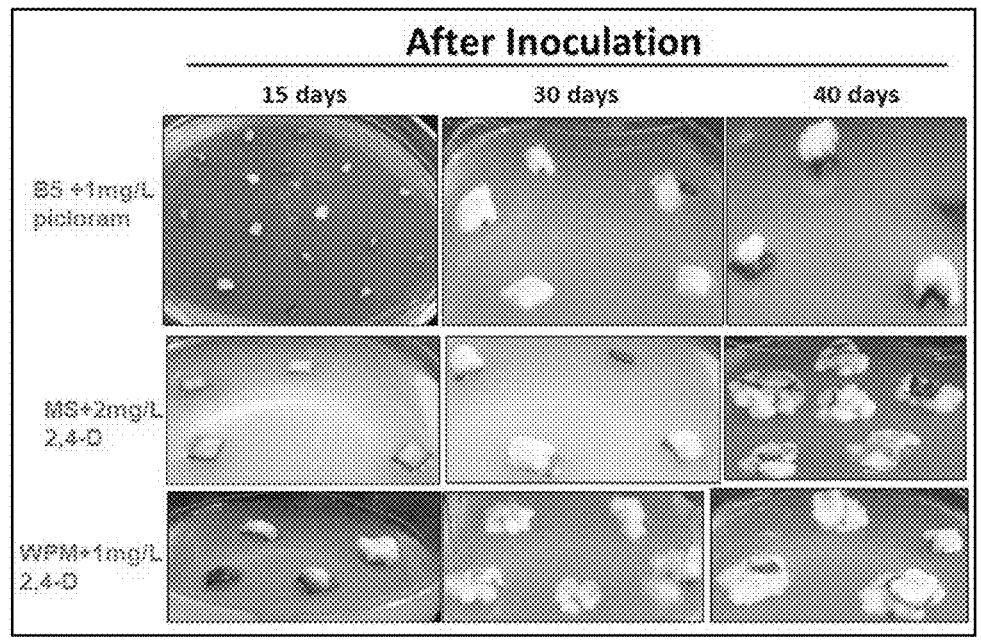
FIG. 3 shows the growth of calli from cambial explants of *T. arjuna*. in different culture medium.

Among the three different media with different PGRs, WPM with 1 mg/L 2,4-D was optimal and shows highest percentage of response (80%) followed by B5 (53%) and MS medium (43%) (FIGS. 2 & 3). The actively proliferating cambium cells were gently separated from the explants and sub-cultured on the same media and maintained without contamination.

Figure 4:
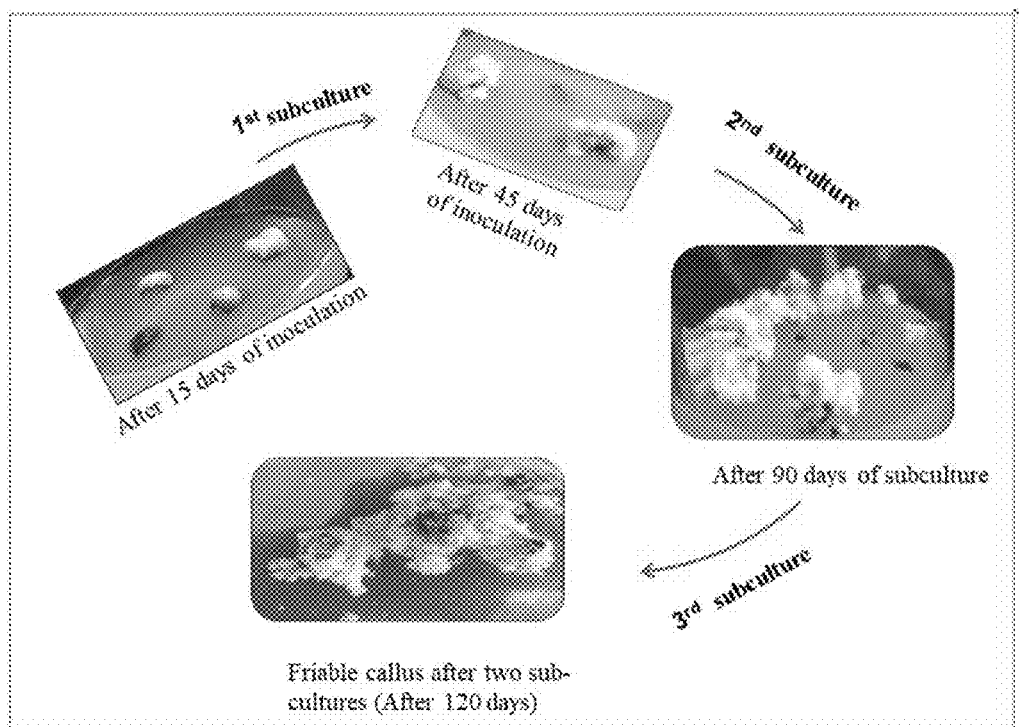
FIG. 4 shows the process of production of friable calli from cambium tissue of *T. arjuna*

Production of Friable Calli:

The callus was produced by using WPM medium supplemented with 1 mg/L 2,4-D was sub-cultured for every four weeks on the same fresh medium. The cells showed the proliferation after 15 days of inoculation and the friable calli were obtained after third subculture (FIG. 4).

Establishment of Suspension Culture:

Initial suspension cultures were established by inoculating approx. 1 g of fresh callus of *T. arjuna* into 250 ml Erlenmeyer flasks containing 100 ml of WPM liquid medium with 1 mg/L 2,4-D and 30 g/L sucrose. The flasks were agitated at 120 rpm, at 25±2° C., ~2500 lux of light and under a photoperiod of 16/8 h (light/dark). After four weeks of incubation period, the cultures were filtered by using 250 µm Nylon (BD Falcon™) filters and used as an inoculum. 20% (v/v) of inoculum was transferred and the growth parameters of suspension culture were recorded at different intervals of time (Table 2).

TABLE 2

Determination of Biomass Growth (fresh weight) of the suspension cell culture of *T. arjuna*

| Media | PGRs | Wet Biomass (mg/ml) at different intervals of time | | | |
|---|---|---|---|---|---|
|  |  | 1st Week | 2nd week | 3rd week | 4th week |
| WPM | 1 mg/L 2,4-D | 12 | 16.5 | 63 | 26.8 |
|  | 1 mg/L 2,4-D + 0.5 mg/L BAP | 10.5 | 12.0 | 23.0 | 14.0 |
|  | 1 mg/L 2,4-D + 0.5 mg/L NAA | 10.4 | 18.0 | 82.0 | 34.0 |
|  | 1 mg/L 2,4-D + 0.5 mg/L KN | 8.4 | 0.6 | 0.5 | 0.5 |
| MS | 1 mg/L 2,4-D + 0.5 mg/L BAP | 6.6 | 16.0 | 20.5 | 8.3 |
|  | 1 mg/L 2,4-D + 0.5 mg/L NAA | 7.1 | 14.8 | 24.0 | 9.1 |
|  | 1 mg/L 2,4-D + 0.5 mg/L KN | 23.3 | 26.8 | 31.0 | 11.5 |

TABLE 2-continued

Determination of Biomass Growth (fresh weight) of the suspension cell culture of *T. arjuna*

| Media | PGRs | Wet Biomass (mg/ml) at different intervals of time | | | |
|---|---|---|---|---|---|
| | | 1$^{st}$ Week | 2$^{nd}$ week | 3$^{rd}$ week | 4$^{th}$ week |
| B5 | 1 mg/L 2,4-D + 0.5 mg/L BAP | 0.4 | 13.0 | 92.3 | 21.0 |
| | 1 mg/L 2,4-D + 0.5 mg/L NAA | 19.0 | 19.7 | 47.3 | 11.4 |
| | 1 mg/L 2,4-D + 0.5 mg/L KN | 9.0 | 21.1 | 47.8 | 11.8 |

Figure 5:
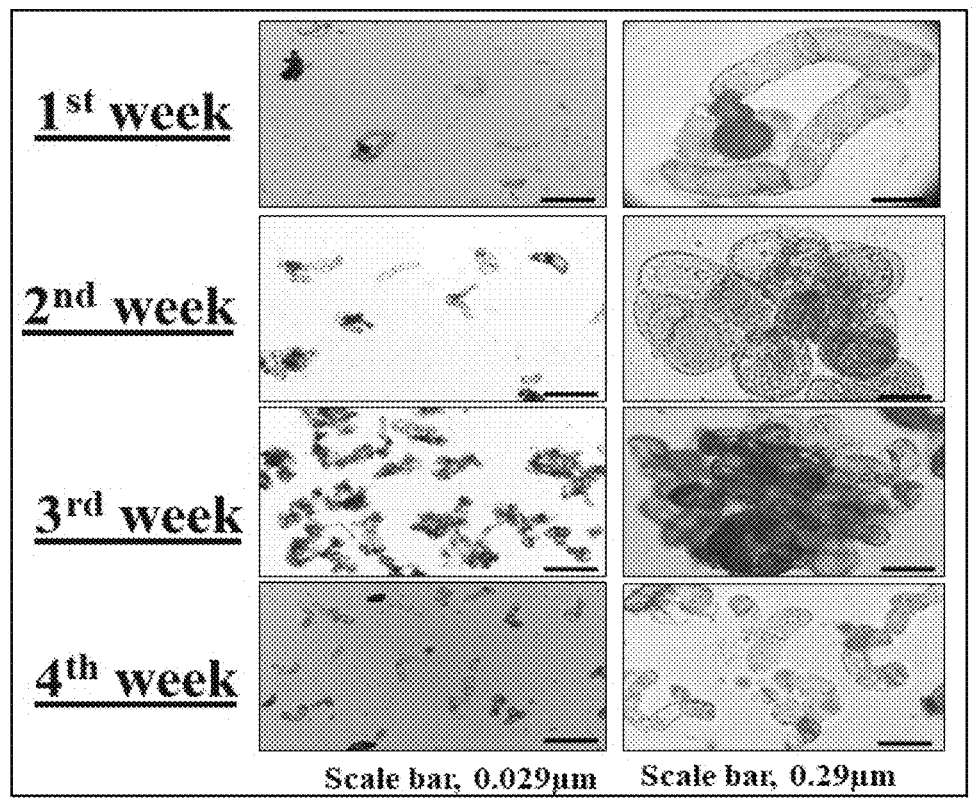
FIG. 5 shows the microscopic observation of suspension culture of *T. arjuna* at different time intervals of incubation (TBO stained).
Figure 6:
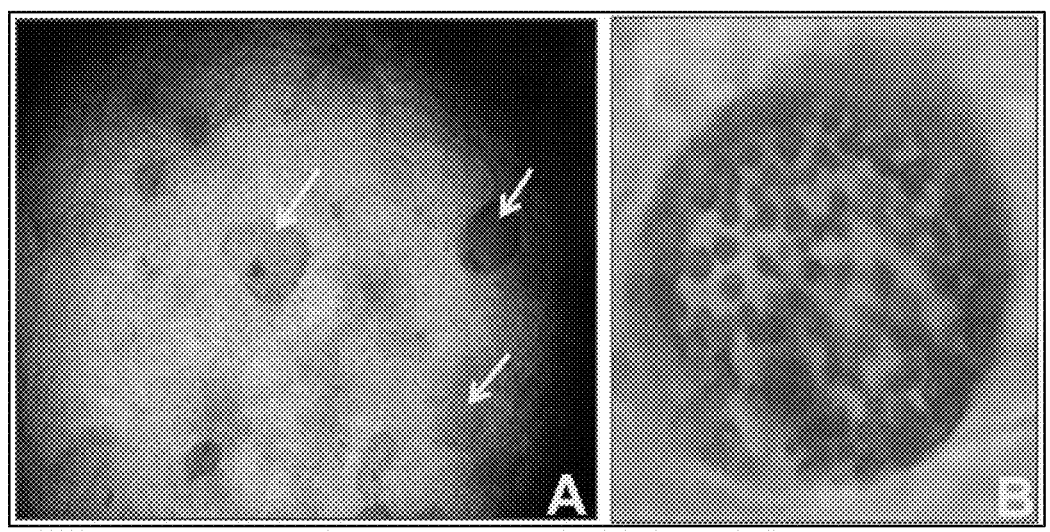
FIG. 6 is a microscopic image showing the confirmation of Cambial Meristematic Cells of *T. arjuna*: A) Cambium meristematic cells from *T. arjuna* suspension culture; B) Enlarged Cambium meristematic cell showing numerous vacuole like structures.

Microscopic Studies of Suspension Culture:

1 ml of suspension culture was collected at different intervals of time as shown in the table 2. 100 µl of suspension cells were transferred to microscopic slide and added one drop of 1% Toluidine blue (TBO). Then after 2 min the slide was washed gently with sterile distilled water to remove over stain and covered with a thin cover slip. Microscopic analysis of the suspension culture of *T. arjuna* cells revealed that the cell elongation and division were observed during the first and second week respectively. The number of cells and biomass were more in third week and cells reached the stationary phase. The biomass was seen to decline after three weeks of incubation and culture turns brown. (FIG. 5). The presence of cambial cells in the suspension culture was confirmed by neutral red dye, which stains the vacuoles in the cell. The suspension culture cells showed many vacuolar structures, this is a characteristic feature of cambial meristematic cells (FIG. 6).

Cryopreservation:

The cryopreservation of suspension culture was carried out as follows: Three weeks of suspension culture was allowed to settle down and the supernatant was removed using a sterile pipette. Then equal volume of pretreated media (1M mannitol in WPM with 1 mg/L 2,4-D culture media) was added to the cells and incubated for 2-3 days with 120 rpm at 25±2° C. in the dark. This culture was kept on an ice tray and the supernatant was again replaced with equal volume of cryoprotectant solution (2M sucrose, 1M glycerol, 1M DMSO and 1% L-proline). The suspension cells along with cryoprotectant solution was incubated 4° C. for 1 h with intermittent shaking. This solution was then dispensed into cryovials, aseptically and was frozen at −80° C. in a deep freezer.

Example 2: Identification and Isolation of Secondary Metabolites

The bark of *Terminalia arjuna* is reported to contain many bioactive compounds like Arjunic acid, Arjunolic acid, Arjungenin, Arjunetin, Arjunoglucoside-I, Arjunoglucoside-II, Asiatic acid, Catechin and Gallocatechin, which can be isolated from the cambium. The following illustrative example shows the isolation of arjunolic acid from the callus of *Terminalia arjuna*.

Analysis of Arjunolic Acid:

1000 mg of dried callus derived from culture media or suspension culture from shake flask or airlift bioreactor (20 mesh-passed raw material) generated from cambium layer of *Terminalia arjuna* was ground using motor and pestle and the sample was extracted with methanol at about 60-65° C. for 1 h, 3 times and the extract was filtered. The filtrate was concentrated to get a dried mass under reduced temperature with high vacuum. A known weight of the sample was subjected to analysis by HPLC and HPTLC for confirmation and quantification of Arjunolic acid. Alternatively, arjunolic acid is also isolated by super critical fluid extraction process (SCFE) which is provided in the below steps:

a) Dried callus derived from culture media or suspension culture from shake flask or airlift bioreactor (20 mesh-passed raw material) and charged into an extractor;

b) Extracting in supercritical fluid $CO_2$ with 200-300 bar pressure along with ethanol 15% w/w entrainer at 45-50° C. for 3-5 hrs to obtain S1 and S2 fractions;

c) Removing the residuals from the S1 fraction and extracting with hexane to obtain a hexane soluble and hexane insoluble layer;

d) Separating the hexane insoluble layer and extracting with ethyl acetate to obtain an ethyl acetate fraction concentrate to half volume;

e) Cooling the ethyl acetate fraction at 5° C. for 12 hours and to obtain arjunolic acid.

Figure 7:
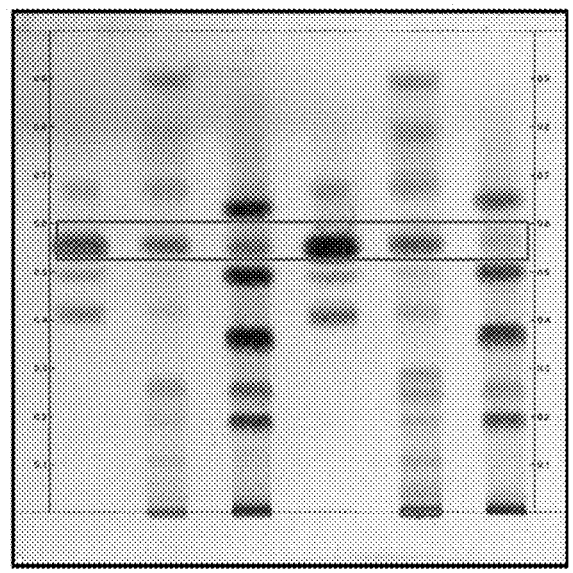
FIG. 7 shows the chromatographic image of HPTLC Profile of Callus Extract for the identification of arjunolic Acid. Lanes 1 and 4 are arjunolic acid standard, lane 2 and 5 are the callus extract and lanes 3 and 6 shows the profile for *T. arjuna* bark extract.
Figure 8:
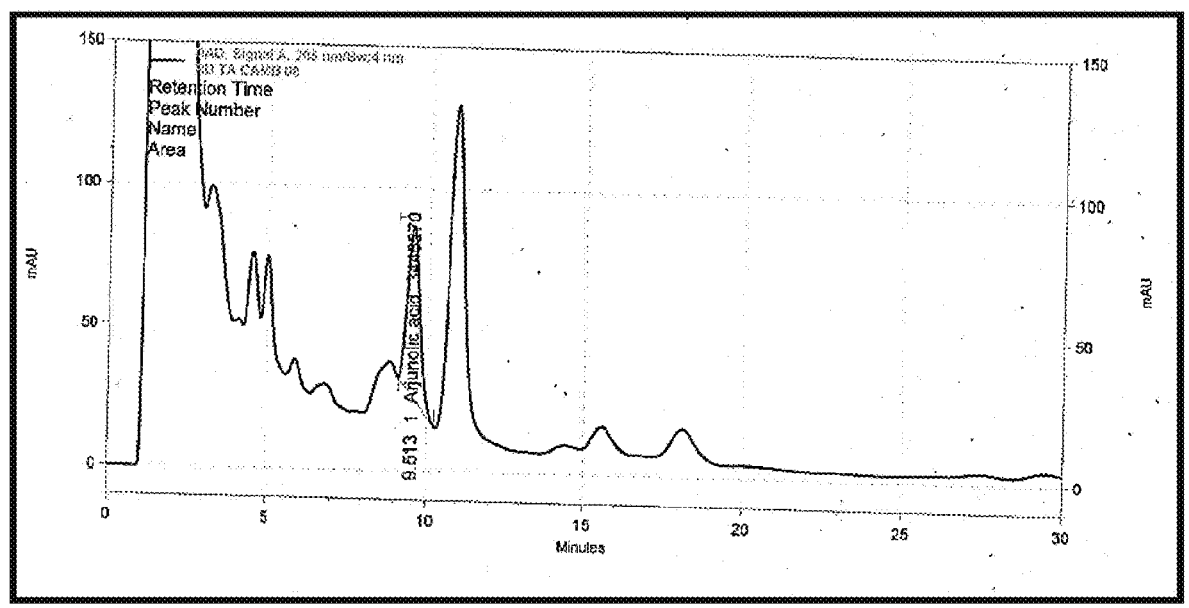
FIG. 8 shows the HPLC chromatogram of arjunolic acid isolated from the cambium callus extract of *T. arjuna*.

The presence of arjunolic acid was confirmed by HPTLC (FIG. 7) and HPLC (FIG. 8)

Testing the Presence of the Arjunolic Acid by HPLC from Suspension Cultured Cells:

Among the three different media with different PGRs, WPM medium supplemented with 1 mg/L 2,4-D showed high assay and content of arjunolic acid on the raw material basis (Table 3).

TABLE 3

Presence of the arjunolic acid in suspension culture cells by HPLC

| | 4th week of suspension culture | | |
|---|---|---|---|
| Media with PGRs | Yield (%) | Assay (%) | On raw material basis (%) |
| MS + 2 mg/L NAA | 9.67 | 0.36 | 0.03 |
| B5 + 1 mg/L Pic | 37.55 | 0.38 | 0.14 |
| WMP + 1 mg/L 2,4-D | 11.43 | 2.6 | 0.30 |

The assay of Arjunolic acid is high in calli (3.5%) derived from cambium tissue followed by suspension culture (2.6%) and bark (0.25%) and on raw material basis there was a five-fold increase of Arjunolic acid production when compared with bark. Moreover, this increased arjunolic acid production was achieved around four weeks in suspension culture whereas it took around four months in callus culture (Table 4&5).

TABLE 4

Arjunolic acid content from *Terminalia arjuna*

| Parameters | Bark Solvent Extraction Method | Bark SCF Extraction Method | Callus derived from Cambium | Cells of callus under Suspension culture |
|---|---|---|---|---|
| Extract Yield % | 24.41% | 30% | 10% | 11.43% |
| HPLC Assay % | 0.25% | 0.30% | 3.5% | 2.6% |
| Arjunolic Acid On Raw Material Basis | 0.06% | 0.09% | 0.35% | 0.3% |

TABLE 5

Arjunolic acid content from suspension culture cells at different time intervals

| Parameters | I Week | II Week | III Week | IV Week |
|---|---|---|---|---|
| MeOH Extract Yield % | 7 | 21 | 23.82 | 10.06 |
| HPLC Assay % | 0.04 | 0.10 | 2.49 | 0.13 |
| Arjunolic Acid On Raw Material Basis | 0.0028 | 0.021 | 0.59% | 0.013 |

The following mentions the important aspects of the invention.

1. The important role of provenance, season and age of cambial tissue determines the yield of callus and the generation of secondary metabolites. Our previous work has established that collection of cambium during its dormancy is much better than in other seasons. (N. Venugopal and K. V. Krishnamurthy, 1987, Seasonal Production of Secondary Phloem in the Twigs of Certain Tropical Timber Trees. Annals of Botany, 60: 61-67; N. Venugopal and K. V. Krishnamurthy, 1987, Seasonal production of secondary xylem in the twigs of certain tropical trees. IAWA Bulletin, 8 (1): 31-40; N. Venugopal and K. V. Krishnamurthy, 1987, Organisation of vascular cambium during different seasons in some tropical timber trees. Nord. J. Bot., 8(6): 631-638). The present invention also used cambium collected during its dormancy.
2. Stem twigs of the size 15 to 20 mm diameter gives the best result
3. Another important aspect is the standardization of the period when the callus must be selected for suspension culture for the maximum content of the desired secondary metabolites. From callus the secondary metabolite content was optimal after a period of 4 months. From the suspension culture the secondary metabolite content was optimal after a period of 2 or 3 weeks for *T. arjuna*. The present invention emphasizes the use of suspension cultures for easy isolation of secondary metabolites. Further, airlift bioreactor based culture of cambium derived callus will result in a continuous supply of cells for the isolation of secondary metabolites. This decreases the need to isolate the metabolites directly from plant sources, is less time consuming and is environment friendly.
4. The invention also discloses a novel method for the extraction of arjunolic acid by Super Critical Fluid Extraction (SCFE) using liquid carbon-dioxide. The yield of arjunolic acid is better than the conventional solvent extraction methods.

The present invention discloses the isolation of secondary metabolites from *Terminalia arjuna* from the calli as well as the suspension cultures derived from cambium. The above process can be used for the isolation of secondary metabolites from *Berberis aristata*, *Oroxylum indicum*, *Pterocarpus marsupium*, *Salacia* sp., *Santalum album*. However, the difference in the characteristic features of the plants, require modifications in the process development of callus, establishment of suspension culture and isolation of secondary metabolites.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of isolating secondary metabolites from the suspension cultures of pluripotent cell line from the callus derived from the cambium of *Terminalia arjuna*, said method comprising steps of:
    a) Washing the *Terrninalia arjuna* twigs (15-20 mm diameter) in tap water followed by Tween 20 wash;
    b) Incubating the washed *Terminalia arjuna* cupola twigs in distilled water containing 10-50 mg/L ascorbic acid for 15-30 minutes, to avoid subsequent phenolic oxidation and browning of callus before its induction;
    c) Treating the twig pieces of *Terminalia arjuna* with disinfecting solution for 1-5 minutes and rinsing in sterile distilled water;
    d) Separating the cambium layer from the treated twigs and inoculating the cambial explants in the culture bottles containing Woody Plant medium combined with 2,4 Dichlorophenoxyacetic acid along with sucrose and agar, with xylem side (phloem side is avoided) in contact with the medium;
    e) Incubating the culture bottles at 23-27° C. under 2,000-2,500 lux of white florescent light for 16 h/day for induction of callus;
    f) Sub-culturing the callus after 15 days of inoculation, followed by a second sub-culture after 45 days of inoculation and third subculture after 90 days of inoculation to yield friable calli after a period of 120 days of inoculation;
    g) Transferring the friable callii into a conical flasks or airlift bioreactor containing culture medium, growth regulators and sucrose maintained at 25±2° C., with a light intensity of ~2500 lux under a photoperiod of 16/8 h (light/dark) with continuous shaking (at 120 rpm) in the conical flasks or aeration in the air lift bioreactor, respectively, for a period of 4 weeks;
    h) Filtering the cultures using 250 μm Nylon filters for use as an inoculum;
    i) Transferring 20% inoculum into individual conical flasks containing liquid Woody Plant media containing 2.4-Dichlorophenoxvacetic acid and incubating at 25±2° C., at 120 rpm, with a light intensity of ~2500 lux under a photoperiod of 16/8 h (light/dark) with continuous shaking for a period of 1-4 weeks for evaluating the biomass production;
    j) Separating the cells after three weeks of incubation and adding equal volume of pre-treated media comprising of 1.0 M mannitol in liquid Woody Plant medium with 2,4-Dichlorophenoxyacetic acid and incubated for 2-3 days with 120 rpm at 25±2° C. in dark;
    k) Separating the cells from the pre-treated culture of step j) and replacing the supernatant with equal volume of cryoprotectant solution comprising 2.0 M sucrose, 1.0 M glycerol, 1.0 M DMSO and 1% L-proline (w/v);
l) Incubating at 4° C. for 1 h with intermittent shaking followed by freezing at −80° C. for long term storage;
m) Separating the cells of step j) after three weeks of culture or re-culturing the frozen cells of step l) and extracting with solvent and/or super critical fluid extraction (SCFE) for the identification of secondary metabolites.

2. The method as in claim 1, wherein the secondary metabolite is selected from the group comprising of Arjunic acid, Arjunolic acid, Arjungenin, Arjunetin, Arjunoglucoside-I, Adunoglucoside-II, Asiatic acid, Catechin and Gallocatechin.

3. A method of isolating Arjunolic acid from the suspension cultures of pluripotent cell line from the callus derived from the cambium of *Terminalla arjuna*, said method comprising steps of:
a) Washing the *Terminalla arjuna* twigs (15-20 mm diameter) in tap water followed by Tween 20 wash;
b) Incubating the washed *Terminalla arjuna* twigs in distilled water containing 10-50 mg/L ascorbic acid for 15-30 minutes, to avoid subsequent phenolic oxidation and browning of callus before its induction;
c) Treating the twig pieces of *Terminalla arjuna* with disinfecting solution for 1-5 minutes and rinsing in sterile distilled water;
d) Separating the cambium layer from the treated twigs and inoculating the cambial explants in the culture bottles containing Woody Plant medium combined with 2,4-Dichlorophenoxyacetic acid along with sucrose and agar, with xylem side (phloem side is avoided) in contact with the medium;
e) Incubating the culture bottles at 23-27° C. under 2,000-2,500 lux of white florescent light for 16 h/day for induction of callus;
f) Subculturing the callus after 15 days of inoculation, followed by a second sub-culture after 45 days of inoculation and third subculture after 90 days of inoculation to yield friable calli after a period of 120 days of inoculation;
g) Transferring the friable callii into a conical flasks or airlift bioreactor containing culture medium, growth regulators and sucrose maintained at 25±2° C., with a light intensity of ~2500 lux under a photoperiod of 16/8 h (light/dark) with continuous shaking (at 120 rpm) in the conical flasks or aeration in the air lift bioreactor, respectively, for a period of 4 weeks;
h) Filtering the cultures using 250 μm Nylon filters for use as an inoculum;
i) Transferring 20% inoculum into individual conical flasks containing liquid Woody Plant media containing 2,4-Dichlorophenoxyacetic acid and incubating at 25±2° C., at 120 rpm, with a light intensity of ~2500 lux under a photoperiod of 16/8 h (light/dark) with continuous shaking for a period of 1-4 weeks for evaluating the biomass production;
j) Separating the cells after three weeks of incubation and adding equal volume of pre-treated media comprising of 1.0 M mannitol in liquid Woody Plant medium with 2,4-Dichlorophenoxyacetic acid and incubated for 2-3 days with 120 rpm at 25±2° C. in dark;
k) Separating the cells from the pre-treated culture of step j) and replacing the supernatant with equal volume of cryoprotectant solution comprising 2.0 M sucrose, 1.0 M glycerol, 1.0 M DMSO and 1% L-proline (w/v);
l) Incubating at 4° C. for 1 h with intermittent shaking followed by freezing at −80° C. for long term storage;
m) Separating the cells of step j) after three weeks of culture or re-culturing the frozen cells of step l) and extracting with methanol followed by concentration for the identification of Arjunolic acid by HPLC, HPTLC or NMR;
n) Separating the cells of step j) after three weeks of culture or re-culturing the frozen cells of step l), dried and charged into the extractor;
o) Extracting in Supercritical fluid $CO_2$ with 200-300 bar pressure along with ethanol 15% w/w entrainer at about 45-50° C. for 3-5 h to obtain S1 and S2 fractions;
p) Removing the residuals from the S1 fraction and extracting with hexane to obtain a hexane soluble and hexane insoluble layers;
q) Separating the hexane insoluble layer and extracting with ethyl acetate to obtain an ethyl acetate fraction and concentrated to half the volume;
r) Cooling the concentrated ethyl acetate fraction at about 5° C. for 12 hours;
s) Identifying the presence of Arjunolic acid using HPLC, HPTLC or NMR.

4. The method as in claim 1, wherein the disinfectant is selected from the group comprising, calcium hypochlorite, sodium hypochlorite, hydrogen peroxide, ethanol, silver nitrate, mercuric chloride, benzalkonium chloride.

5. The method as in claim 1, wherein the inducer and 2,4-Dichlorophenoxyacetic acid is added at a concentration of 1 mg/L.

6. The method as in claim 3, wherein the disinfectant is selected from the group comprising, calcium hypochlorite, sodium hypochlorite, hydrogen peroxide, ethanol, silver nitrate, mercuric chloride, benzalkonium chloride.

7. The method as in claim 3, wherein the 2,4-Dichlorophenoxyacetic acid is added at a concentration of 1 mg/L.

* * * * *